United States Patent [19]

Müller

[11] 4,145,924

[45] Mar. 27, 1979

[54] METHOD AND APPARATUS FOR MEASURING THE FLOW SPEED AND THE GAS VOLUME PROPORTION OF A LIQUID METAL STREAM

[75] Inventor: Stefan Müller, Karlsruhe, Fed. Rep. of Germany

[73] Assignee: Gesellschaft für Kernforschung mbH, Karlsruhe, Fed. Rep. of Germany

[21] Appl. No.: 817,029

[22] Filed: Jul. 18, 1977

[30] Foreign Application Priority Data

Jul. 16, 1976 [DE] Fed. Rep. of Germany ....... 2632042

[51] Int. Cl.² ............................................. G01F 1/58
[52] U.S. Cl. .................................. 73/194 EM; 73/19; 73/194 E
[58] Field of Search ............... 73/194 E, 194 EM, 19, 73/61 LM

[56] References Cited

U.S. PATENT DOCUMENTS

| 2,782,369 | 2/1957 | Werner et al. ............. 73/194 EM X |
| 3,830,095 | 8/1974 | Jaross ........................ 73/19 |
| 3,967,500 | 7/1976 | Forster ...................... 73/194 EM |

*Primary Examiner*—Charles A. Ruehl
*Attorney, Agent, or Firm*—Spencer & Kaye

[57] ABSTRACT

Method and apparatus for measuring the flow speed and the gas volume proportion of a stream of liquid metal wherein a magnetic probe is inserted into the stream of liquid metal and induces a first and second voltage according to Faraday's principle of induction in a first and second predetermined volume of the liquid metal stream, the time sequence of the first and second induction voltages due to speed fluctuations is detected as a measure for the flow speed by means of a first and second pair of electrodes at a known axial spacing L, the travel time $\tau$ of a predetermined volume of liquid metal from the first pair of electrodes to the second pair of electrodes is measured and the flow speed $v = L/\tau$ determined therefrom, and that the induction voltage, which decreases in magnitude with increasing gas volume proportion, is used as a measure for the gas volume proportion in the stream of liquid metal.

10 Claims, 9 Drawing Figures

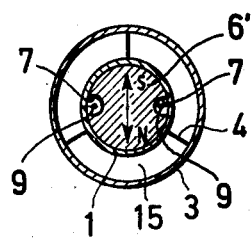
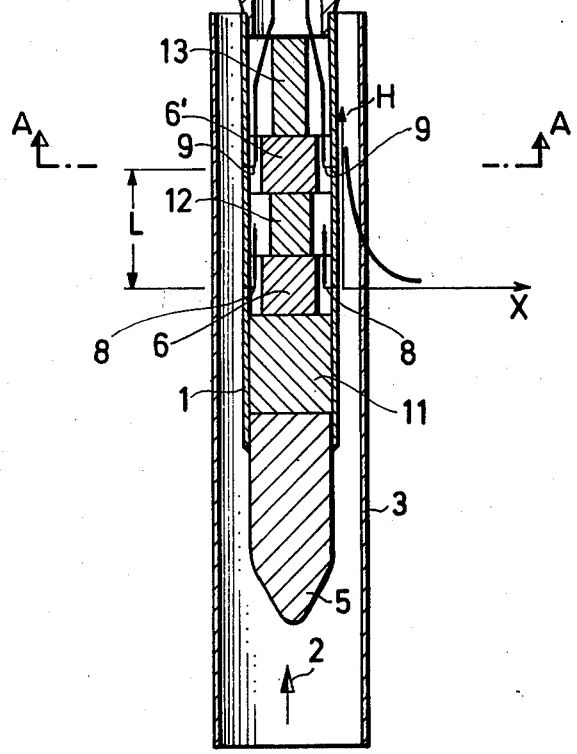

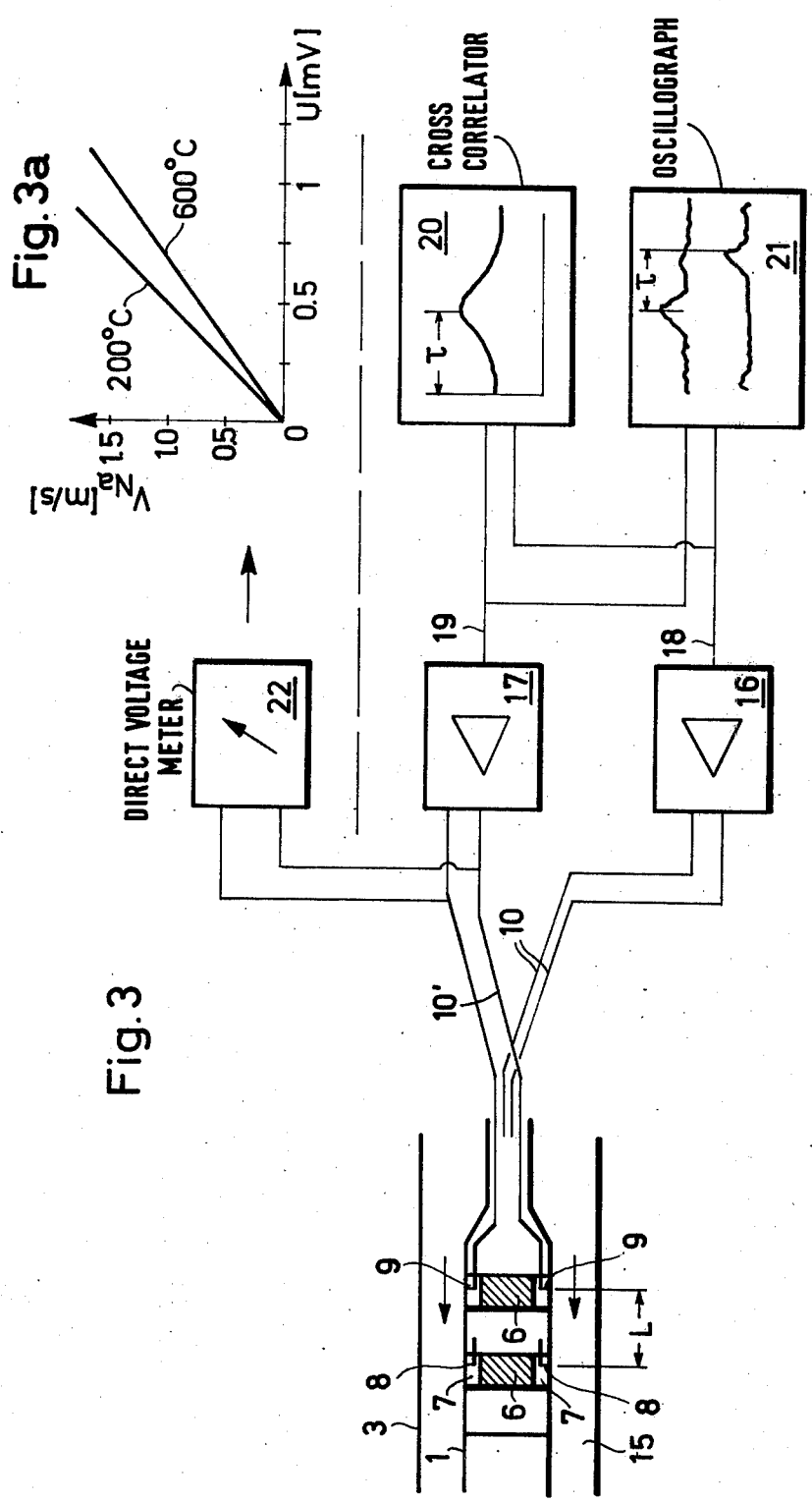

METHOD AND APPARATUS FOR MEASURING THE FLOW SPEED AND THE GAS VOLUME PROPORTION OF A LIQUID METAL STREAM

BACKGROUND OF THE INVENTION

The present invention relates to a method for measuring the flow speed and the gas volume proportion of a stream of liquid metal and to an apparatus for practicing the method.

Such methods and apparatuses gain in significance as the use of liquid metals such as, for example, sodium, as a coolant for nuclear reactors is increased since it is necessary to measure the speed or throughput, respectively, at many components in the system. In particular, it is necessary, in order to avoid local overheating in the area of the fuel elements, for example, as a result of partial blockages, to continuously monitor the stream of liquid metal.

It is also important to detect sufficiently early in time any damage to a fuel rod which becomes evident by a quantity of fission gas being blown into the coolant.

It is known to meet these requirements by arranging the pipeline containing the stream of liquid metal whose speed is to be measured between the pole pieces of a permanent magnet, and to measure the voltage which is induced when a conductor is moved perpendicular to a magnetic field as defined in Faraday's law of induction. (Siemens Magazine Volume 48 (1974), pages 614–617.) Such measuring devices, however, require calibration with temperature dependent characteristics which can be determined only in complicated systems, usually only at the manufacturer's plant. Since the magnetic flux density is included in the measuring result and the field of the permanent magnets changes with age, recalibrations are required which are very complicated to accomplish in the installed state and are often impossible to realize (EUR 1631 d, 1964).

It is further known to perform two-phase current measurements in electrically conducting liquids using Chen probes (see The Review of Scientific Instruments, Vol. 39 (1968) pages 1710–1713), comprising two jacketed thermo-elements which are introduced into the medium to be controlled and whose sensors are welded to the encasing jacket at the point of measurement. The free ends of one sensor are connected with the poles of a stabilized direct voltage source. Changes in conductivity in the region of the Chen probes can be measured as changes in the voltage across the free ends of the other sensor.

However, with such probes it is possible to effect only local measurements within a closely limited region. In order to perform integral measurements, for example, in the plane of an annular chamber, it is necessary to install a plurality of probes over the periphery of the annular chamber. The measuring result is falsified because small gas bubbles flow around the probes and only larger bubbles produce a change in voltage. There is the further drawback that the flow geometry is interfered with by the probes which protrude into the stream and that it is necessary to have available a stabilized external voltage supply.

SUMMARY OF THE INVENTION

It is the object of the present invention to provide a method which makes it possible to measure the flow speed of a stream of liquid metal independent of temperature influences, long-time drifts and gamma radiation influences and to easily calibrate known flow-through meters.

It is a further object of the invention that the method further be usable in a two-phase stream of liquid metal and gas to determine the volume proportion of the gas and the liquid metal.

Finally, it is a further object of the invention to provide an apparatus with which the method for measuring the flow speed and the gas volume proportion of the stream of liquid metal can be realized in a simple manner and which is free of the drawbacks of the known devices.

This is accomplished by the present invention by inserting a magnetic probe into the stream of liquid metal to induce a first and second voltage according to Faraday's principle of induction in first and second predetermined volumes of the stream at an axial spacing L; measuring the time sequence of the variations of the first and second induction voltages due to speed fluctuations as a measure for the flow speed; determining the travel time $\tau$ for said spacing L of a predetermined volume of liquid metal; determining the flow speed v of the stream of liquid metal from the relationship $v = L/\tau$; and utilizing the magnitude of the induction voltage, which magnitude decreases with increasing gas volume proportion, as a measure for the gas volume proportion in the stream of liquid metal.

A surprisingly simple apparatus for practicing this method substantially comprises a magnetic probe having a tubular housing which is closed at its up-stream end and which is inserted and concentrically mounted in a pipe carrying the stream of liquid metal so as to form an annular channel for the passage of the liquid metal. Arranged in the tubular housing or probe tube at a predetermined axial spacing L are two disc-shaped permanent magnets and two pair of electrodes with the two electrodes of each pair being brought through the wall of the probe tube in the center plane of the associated one of the two-disc shaped permanent magnets. The pairs of electrodes are each connected with the inputs of an electronic measured value processor to determine the travel time $\tau$ and hence the flow speed.

According to further features of the invention, it has been found to be of advantage that each of the disc-shaped permanent magnets is magnetized diametrically and is provided at its peripheral edge with two diametrally arranged cutouts, on an axis which is offset by 90° with respect to the magnetic axis, for the electrodes and the lines for connecting the electrodes to the measured value processor. Moreover, preferably the electrodes of the first pair of electrodes are welded in two diametral bores in the wall of the probe tube and, at a predetermined axial spacing L from the first pair of electrodes, the electrodes of the second pair of electrodes are likewise welded in two diametral bores in the wall of the probe tube and are arranged so that the connecting lines of the first and second pairs of electrodes are mutually parallel and extend in the same direction toward the electronic processor.

The advantages realized by the present invention are, in particular, that the flow speed is measured in two spatially closely adjacent flow cross sections as a function of travel time measurements of the speed fluctuations of the stream of liquid metal so that the measuring result is independent of the temperature curve of the probe, the temperature of the flowing liquid metal, long-term drifts, age and influences of gamma radiation.

The same measuring arrangement makes it possible to determine, in synchronism with measurements of the flow speed, the gas volume proportion of a two-phase stream of gas and liquid metal at a limit frequency of several kHz.

BRIEF DESCRIPTION OF THE DRAWINGS

FIG. 1 is an axial sectional view of a preferred embodiment of a measuring probe according to the invention.

FIG. 2 is a radial sectional view along the line A—A of the measuring probe of FIG. 1.

FIG. 3 is a schematic illustration of the measuring probe of FIG. 1 and a block circuit diagram of the measured value processor according to the invention for processing the signals detected by the probe.

FIG. 3a is a graph showing the speed proportional direct voltage which can be obtained from the signals produced by the probe.

DESCRIPTION OF THE PREFERRED EMBODIMENTS

Figure 4:
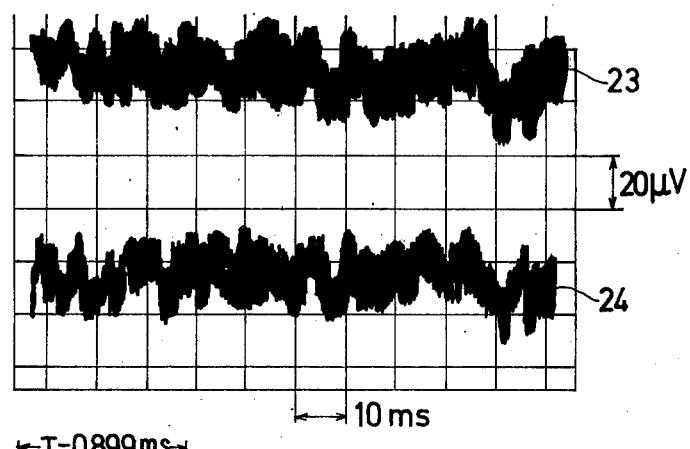
FIG. 4 shows an example of the speed fluctuation signals produced by the arrangement of FIG. 3.

Referring now to FIGS. 1 and 2, there is shown a measuring or magnetic probe according to the invention. It is to be understood that the numerical values set forth below in describing this preferred embodiment of the invention are by way of example only. The magnetic or measuring probe includes a tubular housing or probe tube 1 made of non-magnetic high grade steel which is disposed in a pipe or tube 3 of 12 mm inner diameter in which a stream 2 of liquid metal is flowing. The probe tube 1 is held in concentric relationship with the tube 3 along the longitudinal axis thereof by three bars 4 which are offset by 120°, and is closed at its lower or up-stream end by a welded-on high-grade steel insert 5 of a flow-enhancing shape in order to form an annular flow channel 15 between the probe tube 1 and the pipe 3.

Disposed in the probe tube 1 are two disc-shaped diametrally magnetized magnets 6 and 6' whose center planes are spaced at an axial distance L of 10 mm. Each magnetic disc 6 and 6' has a thickness of 3.5 mm, a diameter of 6.6 mm and is provided along its peripheral edge with two diametrally arranged cutouts 7 on an axis which is offset by 90° with respect to the magnetic axis. The gap between the permanent magnet 6 or 6' and the wall of the probe tube 1 is a maximum of 0.01 mm.

Disposed within the cutouts 7 in the region of the center plane of the disc-shaped permanent magnet 6, are a first pair of electrodes 8 which extend through respective diametral bores in the wall of the probe tube 1. Similarly, a second pair of electrodes 9 is disposed within the cutouts 7 in the center plane of the disc-shaped permanent magnet 6' and extend through further diametral bores in the wall of probe tube 1 so that an axial spacing of L = 10 mm between the two pairs of electrodes results. Each of the electrodes is provided with a connecting line 10 or 10' (only the two connecting lines 10' for the pair of electrodes 9 being shown in FIG. 1) for connecting the electrodes to an electronic measured value processor to be described below. The two pairs of diametral bores for the two pairs of electrodes 8 and 9 are arranged so that the connecting lines 10 from the first electrode pair 8 and the connecting lines 10' from the second electrode pair 9 are mutually parallel and extend in the same direction through the probe tube 1. The probe tube 1 and electrodes 8, 9 are made of a nonmagnetic high-grade steel of the same chemical composition. Preferably each of the connecting lines 10 and 10' is a jacketed or shielded measuring line or cable including a central conductor which is encased by a metal jacket and which is separated from the jacket by a metal oxide layer, and with the central conductor and the jacket being both made of a nonmagnetic high-grade steel, such as V2A. The central conductor of each of the jacketed lines is welded in the associated bore in the wall of probe tube 1 to serve as the respective electrode 8 or 9.

Due to the low conductivity of the wall of probe tube 1 a potential difference arises between the electrode pairs 8 and 9. This difference is measured directly on the wall surface of the probe 1. The electrodes 8 and 9 terminate on the outer surface of the probe tube 1.

The disc-shaped permanent magnets 6 and 6' are made of a magnetic material, such as for example Al-NiCo 450, which is stable up to 600° C. and as shown are held at the desired predetermined distance from each other and from other axially adjacent components of the probe by cylindrical intermediate members 11, 12, 13 which are made of a nonmagnetic material that is heat resistant to at least 600° C. For example, the members 11, 12 and 13 may be made from sintered magnesium oxide or aluminum oxide.

At its upper or down stream end, the probe tube 1 is provided with a guide tube 14 for the leads 10 and 10'.

Each one of the disc-shaped permanent magnets produces a magnetic field in respective volumes of the annular chamber 15 formed between the probe tube 1 and tube 3 and through which the stream of liquid metal 2 flows, with the magnetic field having a field intensity H, as plotted in FIG. 1 over the radius X, and completely penetrating the annular chamber 15. Consequently first and second voltages will be induced according to Faraday's principle of induction by the movement of the liquid metal stream through the associated magnetic fields.

Turning now to FIG. 3, there is shown a simplified block circuit diagram of the measuring device for determining the flow speed of a stream of liquid metal and its proportion of gas volume. The electrodes of the pair of electrodes 8 are connected, via electrode leads 10, with a first amplifier 16 and the electrodes of electrode pair 9 are connected via leads 10' with a second amplifier 17. The voltages induced in the stream 2 of liquid metal as a result of fluctuations in its speed are detected by electrodes 8 and 9. The amplified voltages which constitute the speed fluctuation signals are available at outputs 18 and 19 of amplifiers 16 and 17, respectively.

The outputs 18, 19 are connected with a correlator 20 to form the cross correlation function between the two output signals from the amplifiers 16 and 17 to determine the travel time τ and/or with a rapidly registering signal recorder 21, which may also be an oscillograph, to determine the travel time τ of individual gas bubbles.

One of the pairs of electrodes 8 and 9, the electrodes 9 in the illustrated embodiment, may also be connected with a direct voltage meter 22 with which the speed proportional direct voltage can be compiled slowly and rapidly (intermittent processes). As shown in FIG. 3a, with decreasing temperature of the liquid metal, the slope of the line representing the speed proportional voltage becomes less.

Figure 5:
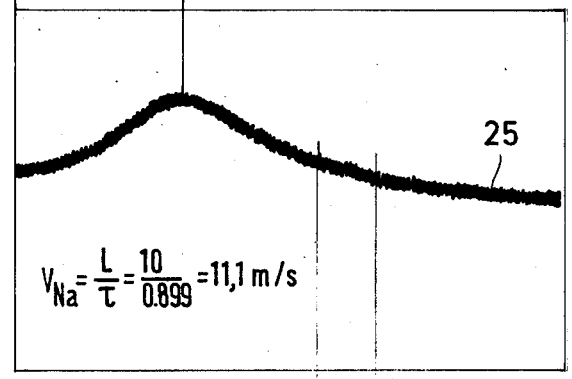
FIG. 5 shows an example of the cross correlation function of the speed fluctuation signals produced by the arrangement of FIG. 3.

FIG. 4 shows an example of the speed fluctuation signals 23, 24, as they occur at the outputs 18, 19 of amplifiers 16, 17 plotted as a function of time while FIG. 5 shows the cross correlation signal 25 generated by correlator 20 from the speed fluctuation signals 23, 24 and indicates the travel time τ of a change in the signal. Such a change in the signal, which may also be caused by a certain gas bubble in the liquid metal, is measured at time 0 at the first electrode pair 8 and at time τ at the second pair of electrodes 9. Since the device described in connection with FIGS. 1 and 2 as the preferred embodiment has its electrode pairs 8, 9 spaced at an axial distance of L = 10 mm, and since the travel time τ = 0.899 is evident in FIG. 5, the average flow speed of the stream of liquid metal $v = L/\tau = 10$ mm/0.899 ms = 11.1 m/s. If desired this flow speed may be automatically determined by a conventional data processing unit connected to the amplifiers 16 and 17 instead of the correlator 20.

Figure 6:
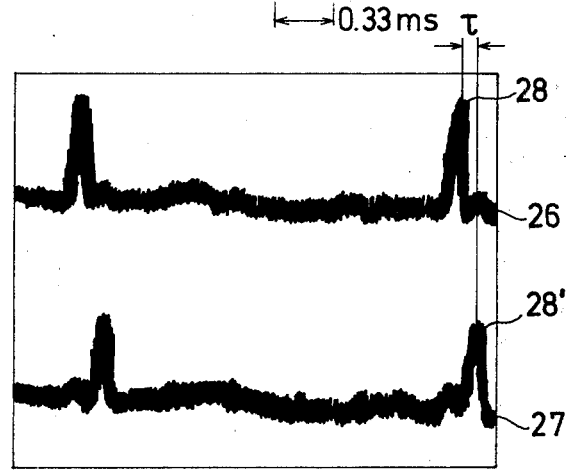
FIG. 6 shows an example of the signals detected and recorded by the arrangement of FIG. 3 from a stream of liquid metal containing individual gas bubbles.

FIG. 6 shows the measured signals 26, 27 of electrode pairs 8, 9 respectively of the measuring arrangement shown in FIG. 1 for a stream of liquid metal containing individual gas bubbles as recorded by an oscillograph 21. Each gas bubble results in a reduction in the voltage induced in the stream of liquid metal 2 which becomes visible as peak 28 or 28'. The time shift between peaks 28 and 28' of two measured signals 26, 27 constitutes the travel time τ from which the flow speed may be determined, again automatically if desired.

Figure 7:
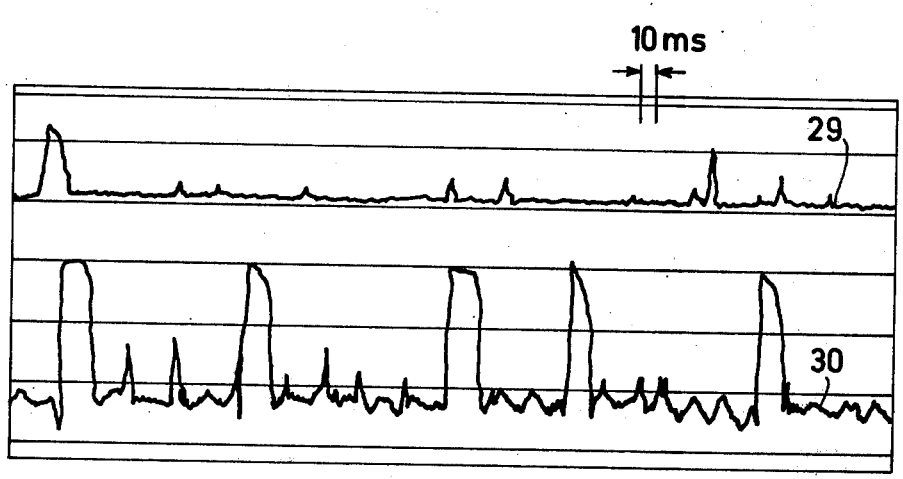
FIG. 7 shows a comparison of the measured signals from a stream of liquid metal having a 20% gas volume proportion utilizing a Chen probe and utilizing a magnetic probe arrangement according to the invention.

FIG. 7 shows the relative signals derived from a stream of liquid sodium having a gas volume proportion of 20% by means of a Chen probe (signal 29) and by means of the apparatus according to the present invention as shown in FIG. 1 (signal 30) with both signals being recorded by the oscillograph 21 of FIG. 3. The recorded strip gives an indication of the gas volume proportion which is accurate to a few percentage points. As is clearly shown the measured signal 29 from the Chen probe shows significantly less signals. This is due to the efficiency of the Chen probe being limited to the immediate vicinity and the fact that smaller gas bubbles flow around the probe.

Figure 8:
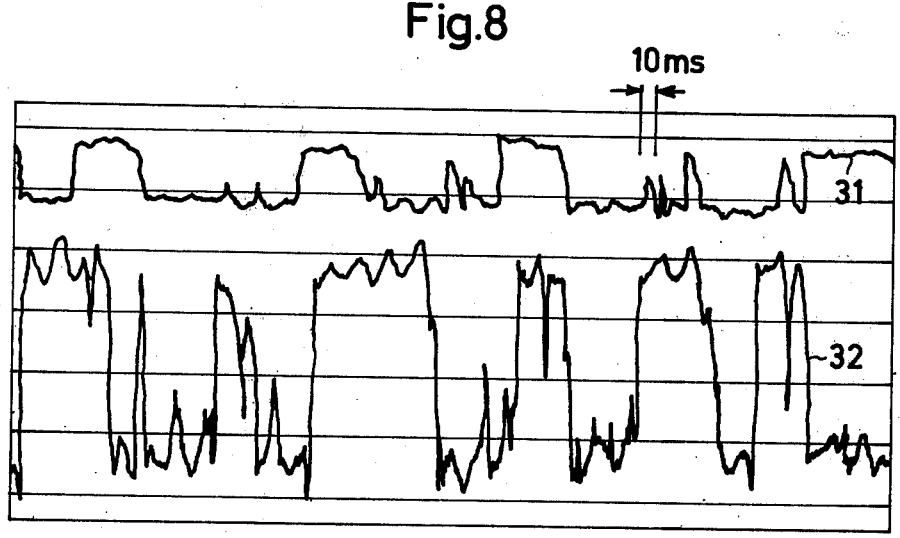
FIG. 8 shows a comparison of the measured signals from a stream of liquid metal having a 55% gas volume proportion utilizing a Chen probe and utilizing a magnetic probe arrangement according to the invention.

FIG. 8 shows a corresponding comparison of the measured signals from a Chen probe (curve 31) with the measured signals from the magnetic probe according to the invention (curve 32) for a gas volume proportion of 55%.

This means that—independent of the amplitude of the measured signals or the scale—the sum of the widths of the peaks, which correspond to the gas volume proportion, occupy about 55% of the viewed section which is determined to be 100%. This is valid for the angular chamber being covered by the magnetic field H (see also the H-X-diagram in FIG. 1).

It will be understood that the above description of the present invention is susceptible to various modifications, changes and adaptations, and the same are intended to be comprehended within the meaning and range of equivalents of the appended claims.

What is claimed is:

1. In an apparatus for measuring the flow speed and the gas volume proportion of a stream of liquid metal flowing in a pipe comprising in combination: a magnetic probe inserted in said pipe and having a tubular housing which is closed at its up-stream end; means for supporting said probe concentrically along the axis of said pipe so as to form an annular channel between said probe and said pipe for the passage of the liquid metal; said magnetic probe including first and second magnetic field generating means for inducing first and second voltages according to Faraday's principle of induction in first and second predetermined volumes of said stream at a spacing L along the axis of said pipe, and first and second pairs of electrodes each associated with one of said first and second magnetic field generating means, for detecting said first and second induced voltages respectively; and electronic measured value processing means, connected to each of said pairs of electrodes, for measuring the time sequence of said first and second induced voltages and for comparing said first and second time sequences to determine the travel time τ of said predetermined volume of liquid metal between said first and second pairs of electrodes whereby the flow speed of the liquid metal is determined from the relationship $v = L/\tau$; the improvement wherein: said first and second magnetic field producing means comprise first and second disc-shaped permanent magnets arranged within said tubular housing transverse to the longitudinal axis of said probe and at said predetermined axial spacing L, and with each of said disc-shaped permanent magnets being diametrally magnetized and provided at its periphery with two diametrally arranged cutouts whose axis is offset by 90° with respect to the magnetic axis; an the two electrodes of each said first and second pair of electrodes extend through said tubular housing in the center plane of the associated one of said first and second disc-shaped permanent magnets, said electrodes and the lines for connecting same to said measured value processing means being disposed in said cutouts.

2. Apparatus as defined in claim 1 wherein the two electrodes of said first pair of electrodes are welded in two diametral bores in the wall of said tubular housing, and wherein the two electrodes of said second pair of electrodes are of the same type as said first pair of electrodes and are welded in two diametral bores in the wall of said tubular housing at said predetermined axial distance (L) from said first pair of electrodes so that the connecting lines for said first pair of electrodes and the connecting lines of said second pair of electrodes are mutually parallel and extend in the same direction toward said measured value processing means.

3. Apparatus as defined in claim 2 wherein said tubular probe housing and each of said electrodes are made of a nonmagnetic high-grade steel of the same chemical composition.

4. Apparatus as defined in claim 3 wherein each of said connecting lines is a jacketed measuring cable whose central conductor and jacket are made of a nonmagnetic high-grade steel; and wherein said central conductor is welded into the bore of the wall of said tubular probe housing to serve as the associated said electrode.

5. Apparatus as defined in claim 4 wherein each of said disc-shaped permanent magnets is made of a magnetic material which is stable up to operating temperatures of 600° C.

6. Apparatus as defined in claim 4 further comprising a plurality of cylindrical intermediate members disposed within said housing for maintaining said disc-shaped permanent magnets at a predetermined distance from one another and from the axially adjacent components of said probe, said cylindrical intermediate members being formed of a nonmagnetic material which is heat resistant to at least 600° C.

7. Apparatus as defined in claim 6 wherein said cylindrical intermediate members are made of sintered magnesium oxide.

8. Apparatus as defined in claim 4 wherein said measured value processing means includes a first amplifier having its inputs connected to the connecting lines for said first pair of electrodes and a second amplifier having its inputs connected to the connecting lines for said second pair of electrodes.

9. Apparatus as defined in claim 8 wherein said measured value processing means further includes correlator means connected to the measuring signal outputs of said first and second amplifiers for determining the cross correlation function of the signal outputs from said first and second amplifiers and said travel time ($\tau$).

10. Apparatus as defined in claim 9 wherein said measured value processing means further includes a rapidly recording measuring instrument connected to said measuring signal output of each of said first and second amplifiers for recording the output signals from said first and second amplifiers to determine the gas volume proportion in said liquid metal stream.

* * * * *